United States Patent [19]
Flores et al.

[11] Patent Number: 6,017,961
[45] Date of Patent: Jan. 25, 2000

[54] KETAMINE AND N-BUTYL-P-AMINOBEZOATE IN PLO

[76] Inventors: John Anthony Flores, 1011 Devonshire #201, Hemet, Calif. 92543; Kenton Lance Crowley, 40970 Alton Ct., Temecula, Calif. 92591

[21] Appl. No.: 09/350,062

[22] Filed: Jul. 8, 1999

[51] Int. Cl.⁷ .................. A61K 31/195; A61K 31/135
[52] U.S. Cl. ............................ 514/561; 514/647
[58] Field of Search ...................... 514/647, 561

[56] References Cited

U.S. PATENT DOCUMENTS 4,599,354  7/1986  Shulman ........................ 514/530
5,817,699  10/1998  Flores et al. ..................... 514/647

*Primary Examiner*—Raymond Henley, III
*Attorney, Agent, or Firm*—Rob L. Phillips

[57] ABSTRACT

The present invention relates to a novel ointment combining Ketamine and n-butyl-p-aminobenzoate (BAB) that is self-administered topically by a subject to alleviate Neuropathic pain, Sympathetic Mediated pain, TMJ pain, SIJ pain and Osteoarthritic pain said subject is experiencing. The present invention is an improvement over the Ketamine only based ointment disclosed in U.S. Pat. No. 5,817,699.

7 Claims, No Drawings

KETAMINE AND N-BUTYL-P-AMINOBEZOATE IN PLO

FIELD OF THE INVENTION

The present invention relates to a method for treating Sympathetic Mediated pain, Neuropathic pain, Myofascial pain, Osteoarthritis pain, Sacro-iliac Joint (SIJ) and TMJ pain with a Ketamine and n-butyl-p-aminobenzoate (BAB) ointment.

BACKGROUND OF THE INVENTION

The attributes of Ketamine are well documented throughout the prior art. U.S. Pat. No. 5,817,699 discloses the benefits of Ketamine in an ointment form relating to the treatment of Sympathetic Mediated pain, Neuropathic pain, Myofascial pain, and Parkinson's disease. The advantages of a topical application of Ketamine are clearly set forth in U.S. Pat. No. 5,817,699. The present invention discloses an ointment combining Ketamine with n-butyl-p-aminobenzoate (BAB). The resultant novel ointment is an improvement over the Ketamine ointment, as disclosed in U.S. Pat. No. 5,817,699, for the treatment of Sympathetic Mediated pain, Neuropathic pain, Myofascial & TMJ pain, and further aids in the treatment of Osteoarthritis & SIJ pain.

Ketamine hydrochloride (2-[o-chlorophenyl]-2-[methylamino] cyclohexone hydrochloride) is an anesthetic, but not in the sense of local anesthetics. Local anesthetics block nerve conduction when applied locally to nerve tissue in appropriate concentrations. A local anesthetic in contact with a nerve trunk can cause both sensory and motor paralysis in the area innervated. Ketamine is a dissociative anesthetic. Dissociative anesthesia is a condition or state of feeling dissociation from the environment by the subject to whom such an agent is administered. Ketamine has traditionally been used as a general anesthetic during induction techniques for surgical or diagnostic procedures. Ketamine's mechanism of action has been compared to that of barbiturates.

Recently there has been growing interest in the role of NMDA (N-methyl-d-aspartate) receptors and their association with Neuropathic pain. NMDA receptors can be found in the hippocampus and cerebral cortex of the brain in addition to the spinal cord. Ketamine has been found to be a potent NMDA receptor antagonist. NMDA receptor antagonists have been found to be very effective in the management of Neuropathic pain.

The administration of Ketamine has usually been via intravenous, oral, subcutaneous or intramuscular routes in order to access venous sites of the NMDA receptors. Ketamine has historically been associated with significant side effects when administered through the aforementioned common routes manifesting as sedative and cognitive impairment. U.S. Pat. Nos. 5,232,950, 5,352,683, 5,543,434 and 5,817,699 disclose the limitations of Ketamine in its common form and applications.

As disclosed in U.S. Pat. No. 5,817,699 studies by the inventors have shown topical Ketamine to be highly effective in the treatment of Neuropathic pain without adversity at doses normally associated with side effects. The pain alleviating benefit of Ketamine has been observed to occur after the onset of side effects (approximately 60 minutes) and dissipate prior to the resolution of side effects (approximately 2 hours). Further studies have shown topical Ketamine to alleviate pain within minutes of application, without proceeding side effects, and to endure for hours to days after a single application.

Studies of an aqueous suspension of n-butyl-p-aminobenzoate, a highly lipid-soluble congener of benzocaine, have been done extensively. The early studies have shown BAB to be quite effective in providing long duration of analgesia via an epidural route in the treatment of intractable cancer pain. The initial impression was that BAB was acting as a neurolytic agent when applied directly to nervous tissue, but subsequent dog studies have shown that not to be the case. Subsequent studies have shown BAB to have long-lasting sensory blockade accompanied by a marked reduction or even absence of pain. It was noted that with the profound sensory blockade, motor, bowel, and bladder function were well preserved. Follow-up studies evaluating BAB's mechanism of action show it to be highly selective for fast sodium channels with little effect on slow sodium channels. This allows BAB to select out C and A-delta nerve fibers, which are responsible for deep achy post injury pain, thus preserving the initial protective nociceptive pain response and motor function of the affected site.

Our clinical studies have demonstrated that when Ketamine and BAB are combined in an ointment for topical use, application to the majority of pain sites has faster and greater analgesic onset than with Ketamine ointment alone. This seems to be particularly true in the management of chronic low back pain. Ketamine ointment has not been found to be effective at all in reducing pain localized to the sacro-iliac joints of the low back. The Ketamine and BAB ointment, however, is able to substantially reduce pain for hours to days.

There also appears to be a comparative difference in the potency of the compounded ointments. This difference must be due to the synergy of the combination. In clinical testing, BAB or Ketamine alone could not generate the pain relief observed with the combination. Most importantly are the added indications of SIJ and Osteoarthritis pain. Ketamine alone was never able to have any positive impact on these two conditions. Also of note is that over time, with Reflex Sympathetic Dystrophy (RSD) in particular, the amount and frequency of dosing to get the same amount of pain relief decreases.

The theoretical advantage of combining Ketamine and BAB is explained by the following mechanism: Ketamine's analgesic properties are due to a link with opioid receptors even though interaction with other receptors (NMDA) and with other neurotransmission systems is also documented. At least part of the analgesic properties are due to interaction with adrenergic, cholinergic, and 5-HT receptors, and voltage-dependent calcium channels. This has a profound affect on local inflammatory response to injury by suppressing sympathetic initiation of the inflammatory reaction and pain. BAB acts on fast sodium channels so that C and A-delta nerve fiber activity is suppressed to prevent post-injury pain. The advantage is that sensory blockade is achieved without loss of motor activity and the protective sensory response to pain, as would occur with other anesthetics.

The advantages of the Ketamine and BAB ointment combination are more fully described under the Summary of the Invention and the Preferred Embodiment sections of this application.

SUMMARY OF THE INVENTION

Accordingly, the present invention relates to a Ketamine and BAB ointment, the composition of which can be topically applied to a subject's pain site thereby rapidly alleviating the subject's pain while avoiding the usual side effects of Ketamine. The ointment disclosed herein is an improvement over the Ketamine ointment disclosed in U.S. Pat. No. 5,817,699.

The primary ingredients in the ointment are Ketamine hydrochloride, n-butyl-p-aminobenzoate, lecithin organogel, ethoxy diglycol, pluronic F-127 gel and deionized distilled water. Ethoxy diglycol is listed as Carbitol® in the Merck Index and lecithin organogel is the combination of the following ingredients in the concentrations similar to those indicated, lecithin soya granular (10 gm), Isopropyl Palmitate, NF (10 gm) and Sorbic Acid, NF-FCC Powder (0.2 gm). Pluronic F-127 gel is a combination of the following ingredients in various concentrations depending on the percentage of Pluronic gel desired: Pluronic F- 127, NF, Potassium Sorbate, NF, and Purified Water, USP.

Other objects, features and advantages of the invention will be readily apparent from the following description of certain preferred embodiments. It is understood that modifications and variations may be effectuated without departing from the spirit and scope of the present invention.

DETAILED DESCRIPTION OF THE PREFERRED EMBODIMENTS

Producing the Ketamine and BAB ointment is accomplished by combining Ketamine hydrochloride, n-butyl-p-aminobenzoate, lecithin organogel, ethoxy diglycol, pluronic F-127 gel and deionized distilled water through a series of steps. The result is a novel topical ointment that improves the Ketamine ointment disclosed in U.S. Pat. No. 5,817,699. The process comprises the steps of:

(a) calculate the amount of Ketamine hydrochloride, based on an overall volume desired necessary to produce a Ketamine and BAB ointment with a Ketamine concentration level between 10 mg/(cc of ointment) –200 mg/(cc of ointment);

(b) calculate the amount of n-butyl-p-aminobenzoate (BAB), based on an overall volume necessary to produce a Ketamine and BAB ointment with a n-butyl-p-aminobenzoate concentration between 50 mg/(cc of ointment)–150 mg(cc of ointment);

(c) dissolve said amount of Ketamine hydrochloride and n-butyl-p-aminobenzoate in 8.5% by volume ethoxy diglycol and 2% by volume hot deionized distilled water;

(d) add suspension from step (c) to between 18% to 32% by volume lecithin organogel;

(e) add to the resultant suspension from step (d) a sufficient amount by volume of pluronic F-127 gel, with a pluronic concentration level between 10% to 40%, ensuring that said desired overall volume is achieved;

(f) mix the solution from step (e) until the pluronic F-127 gel is added and the mixture is evenly distributed. Mixture is then passed through an ointment mill twice to guarantee uniform particle size.

The advantages of Ketamine in an ointment form are disclosed in U.S. Pat. No. 5,817,699. The advantages listed therein are substantially improved with the addition of n-butyl p-aminobenzoate as an active ingredient. The resulting Ketamine and BAB ointment has been used to treat Neuropathic pain and Sympathetic Mediated pain including, but not limited to, carpal tunnel syndrome, abdominal cutaneous neive entrapment syndrome, burns, occipital neuralgia, post herpetic neuralgia, trigeminal neuralgia, phantom limb pain and RSD of the extremities. The Ketamine and BAB ointment has also been used to relieve myofacial pain. In most, if not all, instances the Ketamine and BAB ointment acts faster and with greater analgesic onset than the Ketamine ointment. Additionally, Ketamine and BAB ointment has been found to be effective in treating osteoarthritis and TMJ pain.

The Ketamine and BAB ointment is also highly effective in the management of lower back pain. The Ketamine and BAB ointment is highly effective at reducing pain localized to the sacro-iliac joints of the lower back. The Ketamine ointment disclosed in U.S. Pat. No. 5,817,699 has been found to be ineffective at reducing lower back pain.

As with Ketamine ointment, the Ketamine and BAB ointment also avoids subjecting a patient to the side effects of Ketamine introduced with other routes of administration.

EXAMPLES

1

A 70 year old white female was seen on Feb. 12, 1999 with complaints of bilateral knee pain —left greater than right. She described her pain as being 8 on a Visual Analog Scale (VAS) 0 to 10. She was unable to walk effectively for two days, even with a cane, and was bedridden. She had no unusual rashes, no fever, chills or sweats. Patient suffered no recent changes in her bowels, nausea, vomiting, dysphagia, abdominal pain, and dysuria or ocular or oral lesions.

Past medical history is significant for complaints of progressive knee pain for years. She was diagnosed with degenerative arthritis on Aug. 18, 1997 after an x-ray of her left knee demonstrated moderately severe degenerative changes. The severity of the pain was variable. Some days she was able to walk fairly well, but most times she has marked difficulty and requires the use of a cane. Her knees tended to swell and are usually quite stiff in the morning upon wakening and remains so for 30 minutes. She has tried hot showers and baths without benefit and she has tried various NSAID medications in addition to multiple OTC regimens without pain relief benefit. She is currently unable to use NSAID because of GI upset secondary to hiatal hernia noted by UGI on Nov. 4, 1996.

The patient has been treated with Premarin 0.625 mg qd, Cozaar 50 mg qd, Atenolol 25 mg bid, Voltaren 50 mg tid and HCTZ 50 mg qd. Based on the assessment of moderate to severe osteoarthritis of the left knee with compensatory pain to the right knee the patient was treated as follows:

While the patient was sitting on the examining table, 1 cc of the Ketamine (15%) and BAB (10%) ointment was applied to left knee. A thin strip of the ointment was applied on the medial compartment of the knee and extended inferior to the patella and then to the lateral compartment. The ointment was massaged into the knee by the clinician's gloved hand until completely absorbed. The patient had pain relief 0 (VAS 0 to 10) after 5 minutes and was able to weight bear fully on the left leg. She was also able to ambulate without use of her cane. On four day follow-up, the patient had continued pain relief without reportable side effects. On one month follow-up the patient continues to use the ointment with 3 days of pain relief 0 (VAS 0 to 10) per application without reportable side effects.

2

An 81-year-old white female complained that her lower back was very uncomfortable. She was unable to sleep because of pain. Her upper back discomfort had been more recent. It was centralized on the lower aspect of her neck and refers to her shoulders and head. She described the pain as a burning sensation that becomes achy. She had no referral of pain to her lower extremities. Patient had no bowel or bladder incontinence. Patient had no paresthesias of the upper extremities. Her pain level upon administration was 10 (VAS 0 to 10). She was intolerant to NSAID's because of her hiatal hernia and opiates cause severe constipation problems without relieving her pain.

Patient had a long history of lower back and hip pain dating back to Feb. 12, 1998. X-rays demonstrated degenerative changes of the lumbar spine. Patient was seen by Orthopedics and a lumbar epidural was recommended. The epidural was performed during October of 1998. This did seem to provide some short-term benefit, but the pain began to re-occur and has now progressed to the point of involvement of her upper back. She has massage treatments 2 to 3 times per week performed by her daughter for her back, this also helps but is transient. Patient has been treated with Lescol, Prozac, Tiazac, Ambien, Magnesium Malate, Vitamins E & C, Selenium, Tryptophan, Propulsid, Occuvite, Ginko and Vicodin. Based on the assessment that the 81 year old patient suffered from chronic lower back pain from degenerative changes, and upper back pain due to over compensation from low back problems evidenced from hypertrophy of the muscles without evidence of degenerative changes, the patient was treated as follows:

Medical management was accomplished with use of Ketamine (15%) and BAB (10%) ointment. The ointment was applied from a 30-cc syringe directly to the T-C juncture and bilateral upper trapezium muscles. A total amount of 2 cc was split between the sites and massaged into the skin by the clinician's gloved hand. The patient on initial presentation had a pain level of 10 (VAS 0 to 10). After 10 minutes the pain had dropped to 6 (VAS 0 to 10) and the patient noted greater mobility and was able to stand up straighter as confirmed by direct observation. The patient was contacted 2 days later on follow-up. She was able to confirm continued pain relief of 6 (VAS 0 to 10) without side effects.

3

75-year-old white female complained of bilateral knee pain for almost ten years. She stated that her knees had become quite swollen, almost daily over the past year. Upon awakening in the morning her knees were stiff and painful, which lasted for about 30 minutes before she could carry on with her normal daily activities. She has tried multiple over the counter medications without success in managing the pain. She had been given prescribed NSAID's without significant benefit in pain relief. She was unable to ambulate for more than 50 yards or more than 20 minutes because of pain. She denied trauma to the knees or previous surgery. She had not had any recent falls. Heat to the knees did not seem to provide any degree of relief. Her pain level was 8 (VAS 0 to 10). Patient had been treated with Calan SR 120 mg qd Based on the assessment that the 75-year-old morbidly obese white female with complaints of bilateral knee pain the patient was treated as follows:

While the patient was sitting on the examining table, 1 cc of the Ketamine (15%) and BAB (10%) ointment was applied to each knee. A thin strip of the ointment was applied on the medial compartment of the knee and extended inferior to the patella and then to the lateral compartment. The ointment was massaged into the knee by the clinician's gloved hand until completely absorbed. The patient noted reduction in pain within a few minutes of application. She stated her pain level was 4 (VAS 0 to 10) after 5 minutes and 0 (VAS 0 to 10) after 20 minutes. Extension of the knees improved to 180° and flexion improved, right knee 40°, left knee 40°. The patient was contacted 2 days later after application and reported continued pain relief 0 (VAS 0 to 10) without reportable side effects.

4

A 37-year-old Caucasian female had complaints of marked-to-sever, left-sided facial pain of more than one-year duration. By her report, the pain was felt in the left temporomandibular joint and was greatly exacerbated with jaw movements such as opening, closing and left laterotrusion. The history included four years of painless clicking in the left joint with pain beginning when she was moved from active orthodontic treatment to retainers. She also stated that in the past year, the clicking ceased and was succeeded by sounds of "crackling paper" (crepitus). Other pain symptoms included headache and earache. Additional painless symptoms included subjective hearing loss and a sense of ear fullness.

Using the VAS for pain, she graded her greatest daily pain at 9.8 VAS units and her least daily pain at 9.0 VAS units. She verbally described the intensity of her pain as "Intense", her reaction to the pain as "Unbearable", the pain sensations as multiple ranging from "Piercing to Tingling", and stated that the pain was such that it was "Incapacitating."

Of the twenty sites palpated for pain, five were positive and all these were on the patient's left side, 1) sternocleidomastoid, 2) trapezium, 3) superficial muscles of the cervical spine, 4) deep fibers of the masseter and 5) medial pterygoid (noted as the most painful).

Based upon the complete history and examination, the clinical impression was myofascial pain referring as earache and temporomandibular joint pain. This impression was derived on the basis of those muscles known to refer as earache (deep fibers of masseter, stemocleidomastoid, and medial pterygoid). Treatment therefore was directed to the symptomatic muscles.

Because of the intense level of pain reported by the patient, the decision was made to ignore trigger point (TP) injections. This decision was based upon clinical experience and patient's responses in cases of similar sever pain. The treatment of choice was the topical application of Ketamine and BAB, to the myofascial TPs.

Following the first application of Ketamine and BAB, the patient reported near complete relief of her pain (VAS=<1), which was sustained for over 48 hours with the single application. On day three the patient and husband returned to the clinic for more ointment.

After two days of self-administration of Ketamine and BAB, the patient returned to clinic reporting complete relief of pain. She continued to use Ketamine and BAB for several months and currently has not had any pain return and requires no further treatment to date (15 months).

No side effects or CNS depression were reported during treatment.

5

A 54-year-old, right-handed, white female Bookkeeper began to experience pain in the fingers of her right hand January 1996. While performing a lot of end-of-year manual accounting, the pain worsened, traveling across the right wrist with numbness of her fingers.

On May 1996 she awoke one morning with her entire right arm "frozen." She could not move it without extreme pain. She was evaluated by several general practitioners at Kaiser. Treatment included time off work and NSAID'S without any resolve.

On July 1996 she was diagnosed with tendinitis and placed on physical therapy (PT) for 11 months. EMG studies were performed and were within normal limits. The pain worsened.

On June 1997 a carpal tunnel release was performed on the right hand which resulted in worsening of the pain with a new diagnosis of Reflex Sympathetic Dystrophy (RSD). PT was continued July 1997 through June 1998 with a continued increase in pain and decrease of use of limb. In June 1998 her RSD "crossed over" into her left hand. She continued to seek four other expert evaluations without resolve.

In August 1998 she was placed in a pain management program and advised to obtain nerve blocks or surgery to remove the nerves.

On Jan. 27, 1999 Dr. Flores saw patient in his pain clinic. She was complaining of constant burning pain in different areas of her right hand, with radiating pain up her forearm to the elbow. She noted her fingers do not move and her thumb moves very little with extreme pain. Her right hand was contracted in a claw like appearance, exhibiting mild atrophy and edema. She was exquisitely tender upon exam of the entire hand with allodynia and hyperalgesia. Her pain level on initial evaluation was 10 out of 10 (VAS). The right hand was 2 degrees cooler than left hand and patient was guarding limb.

2 ccs of Ketamine (15%) and BAB (10%) were applied to the dorsal surface of the hand, starting at the wrist and spread distally, coating the surface evenly on each digit without rubbing into the digit. Approximately 30 seconds after application was complete, the patient's VAS of 10 out of 10 dropped to 4 out of 10. Within 15 minutes, VAS dropped to 0, with continued relief for 6 hours at VAS 0. Pain returned to VAS 5 out of 10 at 10 hours and remained there for the following 24 hours.

On follow-up at 48 hours, patient was experiencing continued pain relief with increased mobility of limb and without any side effects.

I claim:

1. A method for treating pain in a subject comprising self-administering topically an ointment containing a concentration of Ketamine between 10 mg/cc–200 mg/cc and a concentration of n-butyl-p-aminobenzoate between 50 mg/cc–150 mg/cc which is sufficient to alleviate pain, but beneath a level to cause side-effects associated with Ketamine.

2. The method according to claim 1, comprising administering a sufficient amount of said ointment to insure a proper dose of Ketamine and n-butyl-p-aminobenzoate to alleviate neuropathic pain.

3. The method according to claim 1, comprising administering a sufficient amount of said ointment to insure a proper dose of Ketamine and n-butyl-p-aminobenzoate to alleviate sympathetic maintained pain.

4. The method according to claim 1, comprising administering a sufficient amount of said ointment to insure a proper dose of Ketamine and n-butyl-p-aminobenzoate to alleviate myofascial pain.

5. The method according to claim 1, comprising administering a sufficient amount of said ointment to insure a proper dose of Ketamine and n-butyl-p-aminobenzoate to alleviate Osteoarthritis pain.

6. The method according to claim 1, comprising administering a sufficient amount of said ointment to insure a proper dose of Ketamine and n-butyl-p-aminobenzoate to alleviate TMJ pain.

7. The method according to claim 1, comprising administering a sufficient amount of said ointment to insure a proper dose of Ketamine and n-butyl-p-aminobenzoate to alleviate SMJ pain.

* * * * *